United States Patent
Hansen (10) Patent No.: US 9,897,694 B2
(45) Date of Patent: Feb. 20, 2018

(54) ULTRASOUND IMAGING PROBE (75) Inventor: Bo Hansen, Copenhagen (DK)

(73) Assignee: B-K Medical Aps, Herlev (DK)

( * ) Notice: Subject to any disclaimer, the term of this patent is extended or adjusted under 35 U.S.C. 154(b) by 741 days.

(21) Appl. No.: 14/232,034

(22) PCT Filed: Jul. 12, 2011

(86) PCT No.: PCT/IB2011/001622
§ 371 (c)(1),
(2), (4) Date: Jan. 10, 2014

(87) PCT Pub. No.: WO2013/008047
PCT Pub. Date: Jan. 17, 2013

(65) Prior Publication Data
US 2014/0133269 A1    May 15, 2014

(51) Int. Cl.
*A61B 8/12* (2006.01)
*G01S 7/52* (2006.01)
*A61B 1/00* (2006.01)
*A61B 8/00* (2006.01)

(52) U.S. Cl.
CPC ...... *G01S 7/52017* (2013.01); *A61B 1/00078* (2013.01); *A61B 8/12* (2013.01); *A61B 8/445* (2013.01)

(58) Field of Classification Search
None
See application file for complete search history.

(56) References Cited

U.S. PATENT DOCUMENTS

| 5,025,778 | A | * | 6/1991 | Silverstein | A61B 1/0008 600/104 |
|---|---|---|---|---|---|
| 5,231,989 | A | | 8/1993 | Middleman et al. | |
| 2002/0087148 | A1 | * | 7/2002 | Brock | A61B 34/20 606/1 |
| 2002/0087166 | A1 | * | 7/2002 | Brock | A61B 34/20 606/130 |

(Continued)

FOREIGN PATENT DOCUMENTS

| EP | 1350471 A1 | 10/2003 |
|---|---|---|
| JP | 02-189139 | 7/1990 |

(Continued)

OTHER PUBLICATIONS

Japanese Office Action dated Apr. 21, 2015, for Japanese patent application No. 2014-519639.

*Primary Examiner* — Luke Ratcliffe
*Assistant Examiner* — Amie M N'Dure
(74) *Attorney, Agent, or Firm* — Anthony M. Del Zoppo, III; Driggs, Hogg, Daugherty & Del Zoppo Co., LPA (57) ABSTRACT

An elongate probe (204) including a probe head (214) with a transducer array (216), a shaft (210) and an articulating member (212). The articulating member is located between the probe head and the shaft. The articulating member is configured to articulate between a position in which the probe head extends along a longitudinal axis of the probe and at least one articulated position in which the probe head extends at a non-zero angle from the longitudinal axis of the probe. The probe further includes a stiffener (224) configured to controllably move from a retracted position to an extended position at which the stiffener inhibits articulation of the articulating member.

19 Claims, 6 Drawing Sheets

(56) References Cited

U.S. PATENT DOCUMENTS

| | | | |
|---|---|---|---|
| 2002/0087169 A1* | 7/2002 | Brock | A61B 34/20 606/139 |
| 2002/0095175 A1* | 7/2002 | Brock | A61B 34/20 606/205 |
| 2007/0027667 A1* | 2/2007 | Osborn, III | A61B 5/1076 703/11 |
| 2007/0178768 A1* | 8/2007 | Harshman | H01R 13/5224 439/660 |
| 2007/0250073 A1* | 10/2007 | Brock | A61B 34/20 606/130 |
| 2007/0250074 A1* | 10/2007 | Brock | A61B 34/20 606/130 |
| 2007/0255291 A1* | 11/2007 | Brock | A61B 34/20 606/130 |
| 2007/0260115 A1* | 11/2007 | Brock | A61B 34/20 600/114 |
| 2008/0009745 A1 | 1/2008 | Hossack et al. | |
| 2008/0119871 A1* | 5/2008 | Brock | A61B 34/20 606/130 |
| 2008/0167560 A1* | 7/2008 | Thornton | A61B 8/12 600/467 |
| 2008/0287802 A1* | 11/2008 | Li | A61B 5/06 600/463 |
| 2008/0287805 A1* | 11/2008 | Li | A61B 8/0833 600/471 |
| 2008/0287860 A1* | 11/2008 | Tgavalekos | A61B 5/06 604/22 |
| 2009/0171191 A1* | 7/2009 | Patrick | A61M 5/1452 600/424 |
| 2009/0171192 A1* | 7/2009 | Patrick | A61M 5/1452 600/424 |
| 2009/0270733 A1* | 10/2009 | Koide | A61B 8/06 600/447 |
| 2009/0270737 A1* | 10/2009 | Thornton | A61B 8/12 600/466 |
| 2010/0179432 A1* | 7/2010 | Thornton | A61B 5/0095 600/463 |
| 2010/0179522 A1* | 7/2010 | Companion | A61B 18/22 606/10 |

FOREIGN PATENT DOCUMENTS

| | | | |
|---|---|---|---|
| JP | 2005-074148 | 3/2005 | |
| WO | 2007028058 A2 | 3/2007 | |
| WO | 2011053773 A2 | 5/2011 | |
| WO | WO 2011053773 A2 * | 5/2011 | A61B 1/00078 |

* cited by examiner

ULTRASOUND IMAGING PROBE

RELATED APPLICATION

This application is a national filing of PCT application Serial No. PCT/IB2011/001622, filed Jul. 12, 2011, published as WO2013/008047 on Jan. 17, 2013. This application claims priority to PCT application Serial No. PCT/IB2011/001622, published as WO2013/008047 on Jan. 17, 2013.

TECHNICAL FIELD

The following generally relates to ultrasound (US) imaging and more particularly to an ultrasound imaging probe that includes a probe head affixed to an articulating member, which is configured to transition between a flexible state in which the articulating member articulates the probe head and a transducer array affixed thereto and a rigid (or non-flexible) state in which the articulating member is inhibited from articulating.

BACKGROUND

Ultrasound imaging has provided useful information about the interior characteristics of an object or subject under examination. A US scanner generally includes a probe with a transducer array that is configured to transmit an ultrasound signal into the object or subject under examination. As the signal traverses the object or subject under examination, portions of the signal are attenuated, scattered, and/or reflected off structure and/or boundaries in the interior of the object or subject, with some of the reflections traversing back towards the transducer array. The later reflections are referred to as echoes and are detected by the transducer array. In B-mode imaging, the echoes correspond to an axial slice through the object or subject and are processed to generate scanlines, which are used to generate a scanplane, or two dimensional image of the slice, which can be displayed via a monitor. B-mode scanplanes can be combined with color flow, Doppler flow, and/or other information.

Figure 1A:
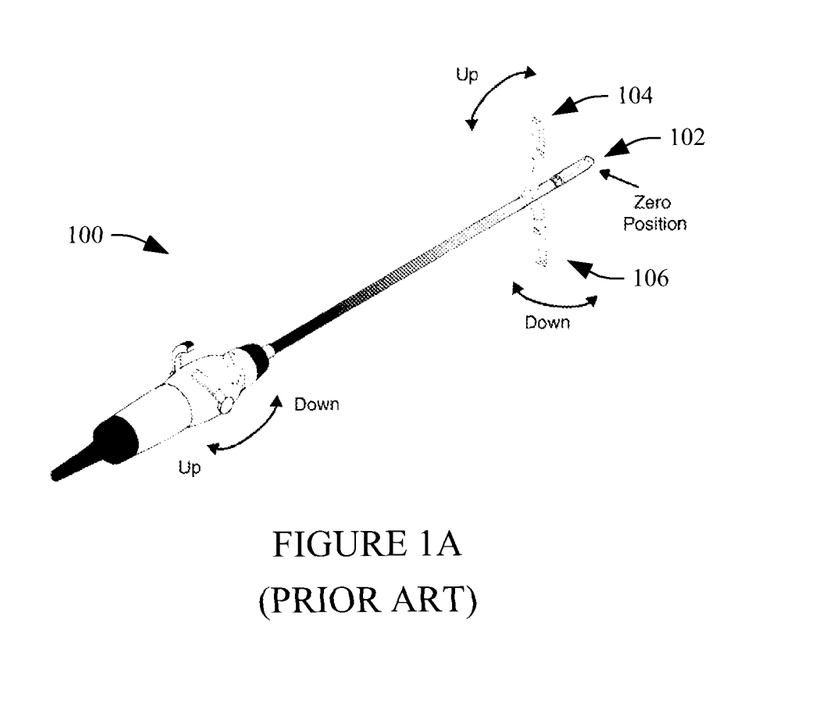
FIGS. 1A and 1B illustrate a prior art ultrasound imaging probe.
Figure 1B:
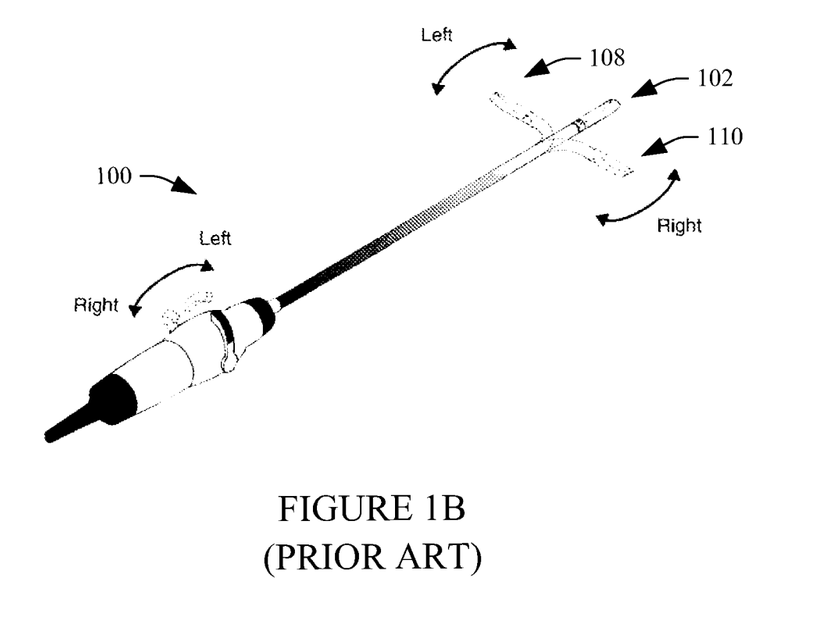

Generally, there are two types of ultrasound imaging probes—flexible and rigid. Flexible ultrasound probes include an articulating portion that can be controllably articulated to move an end of the probe with a transducer array through an angle of up to ninety (90) degrees in one to four planes. FIGS. 1A and 1B show an example of a flexible probe 100; namely, a laparoscopic transducer type 8666, which is a product of BK-Medical ApS, a company of Herlev, Denmark, which is a wholly owned subsidiary of Analogic Corporation, a company of MA, USA. As shown in FIG. 1A, the probe 100 is configured to articulate between a zero position 102 and an up position 104 and a down position 106. As shown in FIG. 1B, the probe 100 is configured to articulate between the zero position 102 and a left position 108 and a right position 110. In contrast, rigid probes are not configured to articulate as such and remain in a single position. Rigid probes, in addition to imaging, can also be used to push, lift, displace and/otherwise maneuver tissue of interest.

Generally, flexible ultrasound probes provide much better access, relative to rigid ultrasound probes, to organs or other tissue of interest for imaging as they are flexible and can be more easily maneuvered in an internal cavity of a patient. Unfortunately, with flexible ultrasound probes, it may not be possible to use the probe to also push, lift, displace and/otherwise maneuver tissue of interest as the probe may inadvertanbly flex while trying to do so, moving the tissue in a manner other than the indended manner and/or not moving the tissue at all.

SUMMARY

Aspects of the application address the above matters, and others.

In one aspect, an elongate probe including a probe head with a transducer array, a shaft and an articulating member. The articulating member is located between the probe head and the shaft. The articulating member is configured to articulate between a position in which the probe head extends along a longitudinal axis of the probe and at least one articulated position in which the probe head extends at a non-zero angle from the longitudinal axis of the probe. The probe further includes a stiffener configured to controllably move from a retracted position to an extended position at which the stiffener inhibits articulation of the articulating member.

In another aspect, a method includes receiving, by a probe, an input that invokes the probe to transition between a first state in which a probe head with a transducer array articulates and a second state a second state in which the probe head with the transducer array is inhibited from articulating In another aspect, an ultrasound imaging system includes a probe and a console. The probe includes a probe head with a transducer array, a shaft, an articulating member, a stiffener, and console interface. The articulating member is located between the probe head and the shaft. The articulating member is configured to articulate between a position in which the probe head extends along a longitudinal axis of the probe and at least one articulated position in which the probe head extends at a non-zero angle from the longitudinal axis of the probe. The stiffener is configured to controllably move from a retracted position to an extended position at which the stiffener inhibits articulation of the articulating member. The console includes ultrasound imaging components and a probe interface. The console and probe interfaces are complementary interfaces, providing an electrical communications path between the probe and the console.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 2:
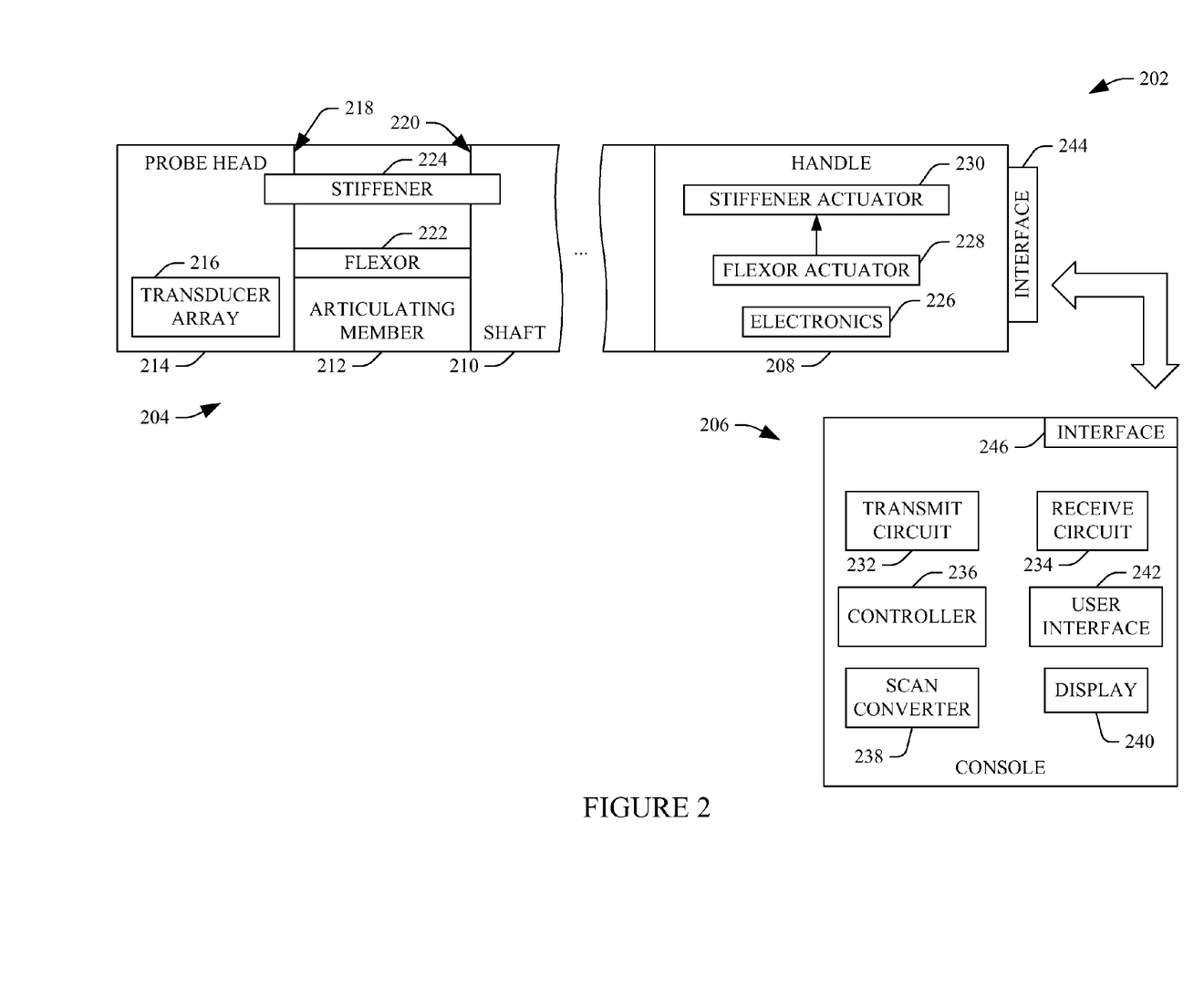
FIG. 2 schematically illustrates an example ultrasound imaging system, including a probe and a console.

FIG. 2 illustrates an imaging system 202 such as ultrasound imaging system. The imaging system 202 includes an ultrasound probe 204 and a console 206. The probe 204 includes a handle 208, a shaft 210, an articulating member 212 and a probe head 214.

The probe head 214 includes a transducer array 216, which includes one or two dimensional array transducer elements. Suitable configurations include, but are not limited to, linear, curved (e.g., convex), and phased arrays. The transducer array 216 can be used to acquire data for A-mode, B-mode, etc. acquisitions, individually and in combination with color flow, Doppler flow, etc.

The shaft 210 extends along a longitudinal axis of the probe 204 and is geometrically configured to allow for moving and/or positioning the probe head 214 (and thus the transducer array 214 attached thereto) within a cavity, such as the abdomen or other cavity of a human patient, or a cavity of an object.

The articulating member 212 is a generally flexible section of the probe 204. A first side 218 of the articulating member 212 is affixed to the probe head 214 and an opposing side 220 of the articulating member 212 is affixed to the shaft 210. The articulating member 212 includes a flexor 222, which is controlled to flex the articulating member 212 to position the transducer array 214 between various positions in one to four planes through angles of up to ninety (90) degrees. Examples of suitable positions include, but are not limited to, one or more of straight (zero), up, down, left and rights positions, for example, such as those shown in connection with FIGS. 1A and 1B.

The stiffener 224 is a general rigid (or non-flexible) member. In the illustrated embodiment, a stiffener 224 is shown spanning across the probe head 214, the articulating member 212 and the shaft 210. As described in greater detail below, the stiffener 224 is controllably moveable at least between a position in which the stiffener 224 does not cross the articulating member 212 and a position in which the stiffener 224 crosses the articulating member 212. This allow for transitioning the probe 204 between at least two states: one state in which the articulating member 212 can be flexed as discussed herein and one in which the articulating member 212 is not flexible.

The handle 208 includes electronics 226, a flexor actuator 228 and a stiffener actuator 230. The electronics 226 are in electrical communication with the transducer array 216 and are used to convey signals to the transducer array 216 that actuate the transducer elements therein to produce ultrasound signals and receive signals therefrom corresponding to received echoes. Alternatively, the electronics 226 can reside outside of the probe 206, for example, in connection with console 206 and/or elsewhere. The flexor actuator 228 is configured actuate the flexor 222. Various approaches can be utilized to actuate the flexor 222. An example of a suitable approach is used in connection with the laparoscopic transducer type 8666. The flexor actuator 228 includes a mechanical and/or electrical mechanism for inhibiting stiffener 224 actuation in response to the articulating being in a non-zero position.

The stiffener actuator 230 is configured to actuate the stiffener 224 to move the stiffener 224 at least between the above two noted states. The stiffener actuator 230 may include a mechanical based and/or an electrical based drive system or mechanism to actuate the stiffener 230. For example, in one instance, a lever, slide, button, knob, or the like is used to move the stiffener 224 between the at least two positions. In another example, a motor and drive or the like is used to move the stiffener 224 between the at least two positions. For the latter, the electronics 226 and/or other electronics can be used to control the motor. The stiffener actuator 230 may be inhibited from actuating the stiffener 224 by the flexor actuator 228 and/or otherwise.

It is to be appreciated that the probe 204 can be used for laparoscopic, endoscopic, and/or other applications, and can be used to assist personnel, for example, with an interventional procedure such as a liver, gall bladder, tumor biopsy, etc., guide personnel, for example, with RF ablation, chemical injection, etc. and/or otherwise. As shown, the probe 204 is employed with the console 206. In other embodiments, the probe 204 can be employed with other consoles.

The console 206 includes a transmit circuit 232 that controls the phasing and/or time of actuation of the individual elements of the transducer array 216, which allows for steering and/or focusing the transmitted beam from predetermined origins along the array and at predetermined angles.

The console 206 further includes a receive circuit 234 that receives signals indicative of the echoes received by the transducer array 216. For B-mode and/or other applications, the receive circuit 234 can beamform (e.g., delays and sums) the echoes into a sequence of focused, coherent echo samples along focused scanlines of a scanplane. The receive circuit 234 and/or other circuitry can be used to process the scanlines to lower speckle and/or improve specular reflector delineation via spatial compounding, and/or perform other processing such as FIR filtering, IIR filtering, etc.

A controller 236 controls the transmit circuit 232 and/or the receive circuit 236. Such control may include, but is not limited to, controlling the frame rate, number of scanline groups, transmit angles, transmit energies, transmit frequencies, transmit and/or receive delays, etc.

A scan converter 238 scan converts the frames of data to generate data for display, for example, by converting the data to the coordinate system of the display. This may include changing the vertical and/or horizontal scan frequency of signal based on the display. Furthermore, the scan converter 238 can be configured to employ analog and/or digital scan converting techniques. A display 240 can be used to present the rendered data.

A user interface 242 includes various input and/or output devices for interacting with the controller 236, for example, to select a data processing and presentation mode, a data acquisition mode (e.g., B-mode), initiate scanning, etc. The user interface 242 may include various controls such as buttons, knobs, a keypad, a touch screen, etc. The user interface 242 may also include various types of visual (e.g., LCD, LED, etc.) and/or audible displays.

In the illustrated embodiment, the probe 204 and the console 206 respectively include complementary electrical interfaces 244 and 246, which can be electrically connected via a cable, wireless communication, or the like. The electrical connection there between allows electrical signals to be conveyed back and forth between the probe 204 and the console 206.

It is to be understood that the relative size, shape and position of the various components 204-246 of the system 202 are provided for explanatory purposes and are not limiting. In other embodiments, at least one of the size, shape and position of at least one of the components is different.

FIGS. 3, 4, 5, 6, 7 and 8 schematically illustrate various examples of the stiffener 224 in connection with the probe 204.

Figure 3:
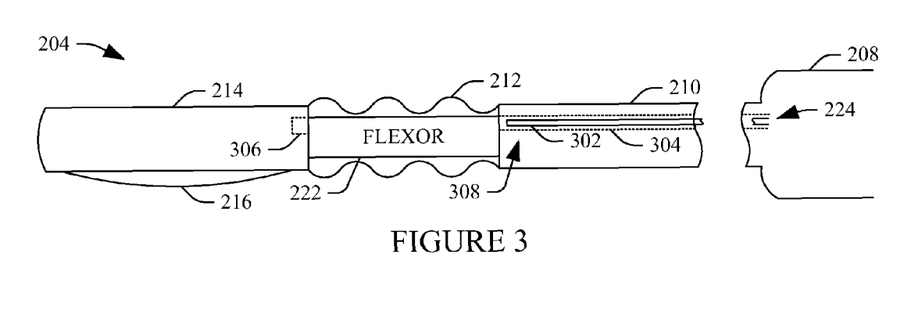
FIGS. 3 and 4 schematically illustrate a first non-limiting example of an articulating member stiffener of the probe.
Figure 4:
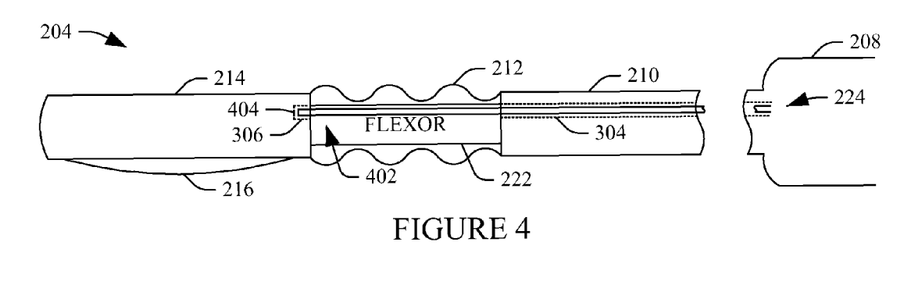

FIGS. 3 and 4 schematically illustrate an example of the stiffener 224 in which the stiffener 224 is driven from the handle 208. In this embodiment, the stiffener 224 includes an elongate rigid bar or rod 302, the shaft 110 includes a material free region or elongate channel 304 in which the stiffener 224 can slide back and forth along the long axis of the probe 204, and the probe head 214 includes a material free region or elongate channel 306 in which the stiffener 224 can slide back and forth along the long axis of the probe 204. The channel 304 extends into the handle 208 as shown. (The channels 302 and 304 can be considered as a single or multiple channels.)

In FIG. 3, the stiffener 224 is positioned such that the stiffener 224 is in a first or retracted position 308 where none of the stiffener 224 is in the articulating member 212. When in this position, the flexor actuator 228 (FIG. 2) can be invoked to actuate the flexor 222 to flex the articulating member 212 up, down, left or right (e.g., as shown in FIG. 1). In FIG. 4, the stiffener 224 is positioned such that the stiffener 224 is in a second or extended position 402 where the stiffener 224 extends from the handle 208 through the flexor 222, and an entire length of the articulating member 212 to the probe head 214. In this position, the stiffener 224 inhibits flexing of the articulating member 212. In this embodiment, an end 404 of the channel 306 provides a mechanical stop 404.

Optionally, in either or both of the positions 308 and 402 of FIGS. 3 and 4, the stiffener 224 can be releasably secured in place.

Figure 5:
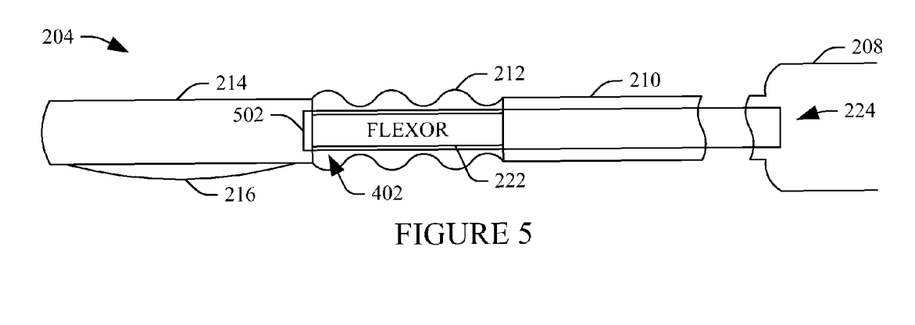
FIG. 5 schematically illustrates another non-limiting example of an articulating member stiffener of the probe.

FIG. 5 schematically illustrates another example of the stiffener 224 in connection with the probe 204. In this embodiment, the stiffener 224 includes a tubular structure 502. In FIG. 5, the stiffener 224 is the extended position. In this position, the stiffener 224 surrounds the flexor 222 (unlike the rod 302 in FIG. 3, which extends through the flexor 222) and inhibits flexing of the articulating member 212. In the retracted position, the stiffener 224 does not extend into the articulating member 212.

Figure 6:
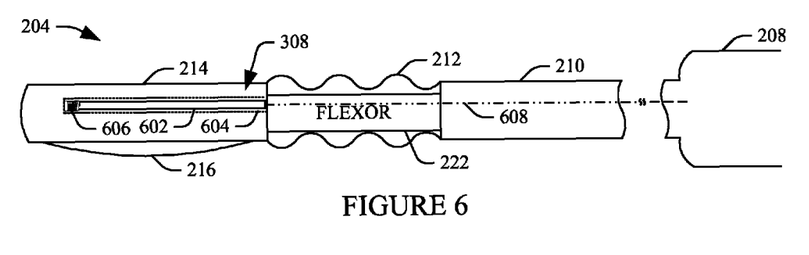
FIGS. 6 and 7 schematically illustrate yet another non-limiting example of an articulating member stiffener of the probe.
Figure 7:
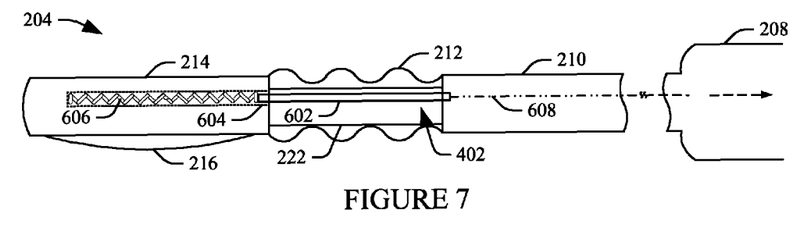

FIGS. 6 and 7 schematically illustrate another example of the stiffener 224 in which the stiffener 224 is driven from the probe head 214. In this embodiment, the stiffener 224 includes an elongate rod 602, which is held in a material free region or elongate channel 604 of the probe head 214 via a pre-loaded elastic device 606 such as a tension spring or the like affixed to one end of the stiffener 224. An element 608 such as a wire, string, cable, or the like is affixed to the other end of the rod 602. The element 608 extends through the articulating member 212, the shaft 210 and the handle 208.

To actuate the stiffener 24, the element 608 is moved in a direction from the probe head 214 to the handle 208, which pulls the stiffener 224 into the articulating member 212 against the pre-loading of the elastic device 606. In FIG. 6, the stiffener 224 is in the retracted position where none of the stiffener 224 is in the articulating member 212, and in FIG. 7, the stiffener 224 is in the extended position where the stiffener 224 extends from the probe head 214 through the articulating member 212 to the handle 208. In this position, the stiffener 224 inhibits flexing of the articulating member 212.

In a variation of FIGS. 6 and 7, the elastic device 606 includes a pre-loaded compression spring or the like which can be used to urge the stiffener 214 into the articulating member 212.

Figure 8:
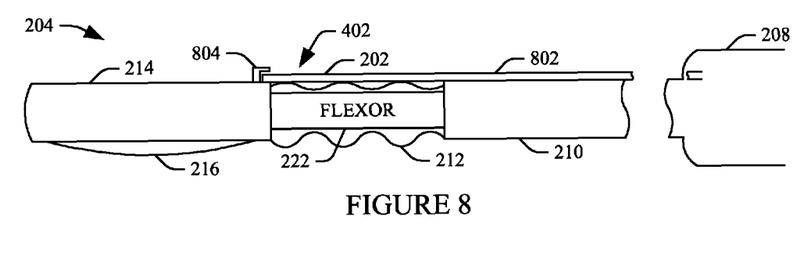
FIG. 8 schematically illustrates still another non-limiting example of an articulating member stiffener of the probe.

In FIG. 8, the stiffener 224 is substantially similar to that stiffener 224 described in connection with FIGS. 3 and 4 except that a bar or rod 802 is located partially outside of the probe 204 and spans an exterior of the probe 204 when in at least the extended positions. (In FIGS. 3 and 4, and FIGS. 5-7, the stiffener spans an interior of the articulating member.) As shown in FIG. 8, this may include sliding the rod 802 along an outer surface of the articulating member 212. A mechanical stop 804 such as a bracket or the like is located on the probe head 214 and provides a mechanical stop for the stiffener 224 and/or holds the stiffener 224 in place.

FIGS. 9, 10, 11 and 12 illustrate various non-limiting examples of the stiffener actuator 230 in connection with the stiffener 224 in connection with mechanical and/or electrical based drive systems 900 and 1100.

Figure 9:
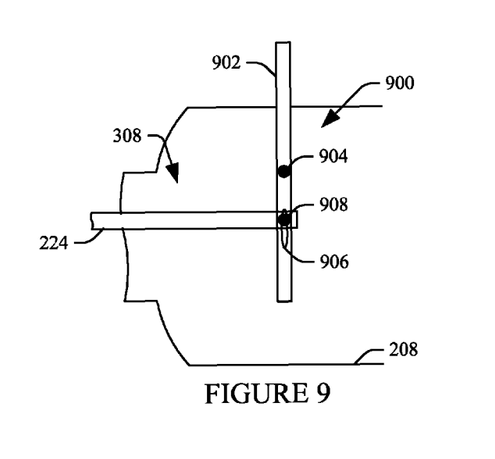
FIGS. 9 and 10 schematically illustrate a non-limiting example of a stiffener actuator of the probe.
Figure 10:
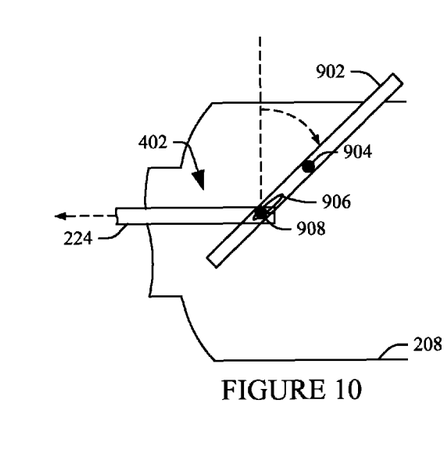

In FIGS. 9 and 10, the stiffener actuator 230 includes a t member 902 such a lever, switch or the like, which is pivotably mounted at a mid-region to a pivot 904 and is configured to pivot about the pivot 904 between at least two positions, which correspond to the retracted and extended positions 308 and 402 of the stiffener 224 discussed in connection with FIGS. 2-8. One end of the member 902 extends out of the handle 208 and the other end is within the handle 208. The member 902 further includes a slot 906 located on a portion of the member 902 in the handle 208. The end of the stiffener 224 is rotatably affixed to the member 902 via a fastener 908 such as rivet, a screw, a bolt, or the like.

In FIG. 9, the member 902 is positioned such that the stiffener 224 in the retracted position 308. In FIG. 10, to move the stiffener 224 to the extended position, the user of the probe 224 pivots the member 902 in a direction away from the probe head 214. As the member 902 pivots as such about the pivot 904, the fastener 908 slides down the slot 906 in the lever 902 towards the probe head 214, urging the stiffener 224 towards the probe head 214 from the retracted position to the extended position in which the articulating member 216 is inhibited from flexing.

Figure 11:
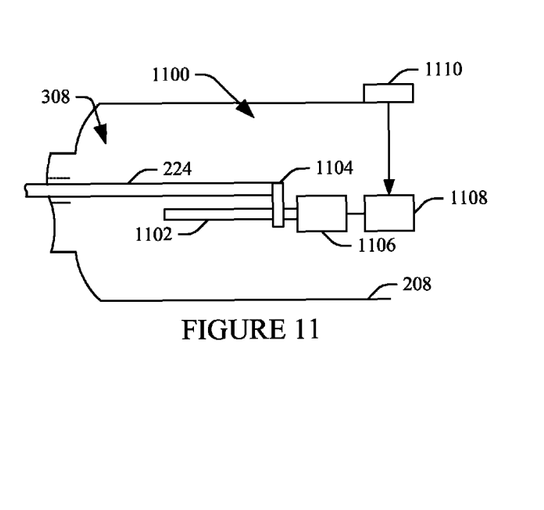
FIGS. 11 and 12 schematically illustrate another non-limiting example of a stiffener actuator of the probe.
Figure 12:
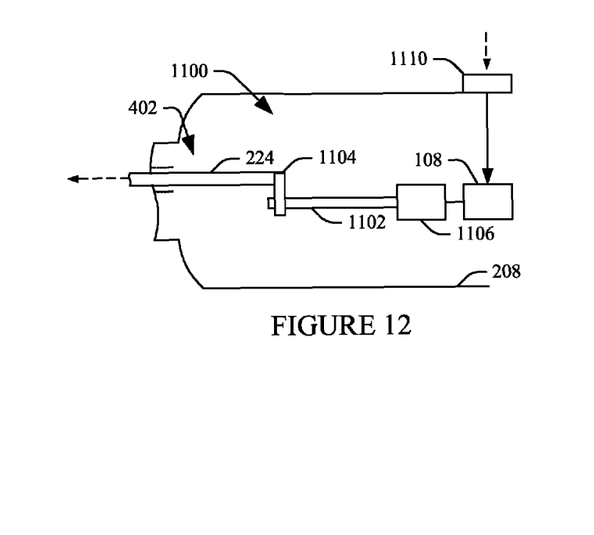

In FIGS. 11 and 12, the stiffener actuator 230 is attached to a drive mechanism 1102 such as a lead, ball, etc. screw or the like via a coupling 1104. A motor 1106, under control of a controller 1108, drives the mechanism 1102, and a switch 1110 actuates the controller 1108. In FIG. 11, the stiffener 224 is in the retracted position 308. In FIG. 12, to move the stiffener 224 to the extended position 402, the user actuates the switch 1110 which conveys a signal to the controller 1108 to drive the motor 1106 to advance the stiffener 224 into the articulating member 212 via the drive mechanism 1102 and coupling 1104.

Figure 13:
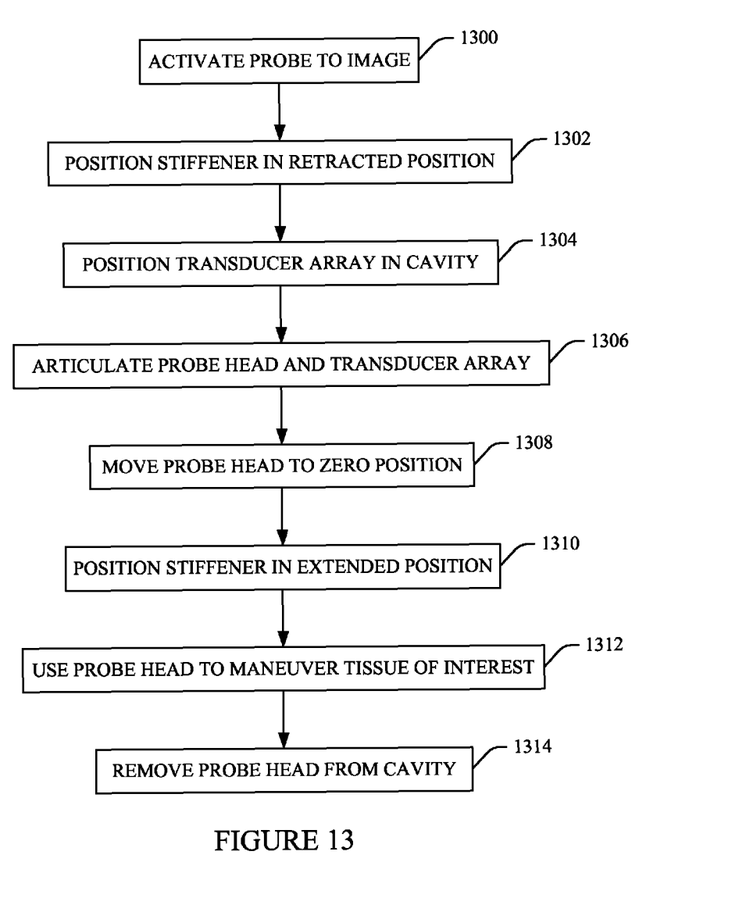
FIG. 13 illustrates an example method.

FIG. 13 illustrates a method for employing the probe 204.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 1300, the probe 204 is activated for ultrasound imaging. In one instance, for this, the probe 204 receives an input invoking the probe 204 to activate.

At 1302, the stiffener 224 is positioned in the retracted 306 position, if not already in the retracted 306 position. In one instance, for this, the probe 204 receives an input invoking the stiffener 224 to move to the position, if not already there.

At 1304, the probe head 214 and hence the transducer array 216 is positioned in a cavity of a subject or object. Generally, the probe head 214 is initially advanced into the cavity through an opening of a trocar or other port into the cavity by an ultrasonographer, ultrasound technologist, ultrasound technician, physician, other authorized personnel, and/or robot.

At 1306, the probe head 214, and hence the transducer array 216, is articulated (e.g., up, down, left and/or right) from the home position as needed by the operator of the probe 204. In one instance, for this, the probe 204 receives an input invoking the articulating member 212 and hence the probe head 204 to articulate.

At 1308, the probe head 214 is moved to the zero position. In one instance, for this, the probe 204 receives an input invoking the probe head 214 to move to the zero position.

At 1310, the stiffener 224 is moved to the extended position 402. In one instance, for this, the probe 204 receives an input invoking the stiffener 224 to move to the extended position 402.

At 1312, the probe head 214 is used to maneuver (e.g., push, lift, displace, etc.) tissue of interest.

Acts 1302-1312 can be repeated, a desired and/or needed.

At 1314, the probe head 214 is removed from the cavity.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An elongate probe, comprising:
   a probe head, including:
      a transducer array; and
      a stiffener;
   a shaft; and
   an articulating member located between the probe head and the shaft, wherein the articulating member is configured to articulate between a position in which the probe head extends along a longitudinal axis of the probe and at least one articulated position in which the probe head extends at a non-zero angle from the longitudinal axis of the probe,
   wherein the stiffener is configured to controllably move from a fully retracted position where the stiffener is entirely in the head to an extended position where the stiffener is concurrently located in the head, the articulating member and the shaft, which inhibits articulation of the articulating member.

2. The probe of claim 1, wherein in the retracted position, the stiffener does not inhibit articulation of the articulating member.

3. The probe of claim 1, wherein in the extended position, the stiffener physically spans at least the articulating member.

4. The probe of claim 3, wherein in the stiffener physically spans an interior of the articulating member.

5. The probe of claim 3, wherein in the stiffener physically spans an exterior of the articulating member.

6. The probe of claim 1, further comprising:
   a stiffener actuator configured to move the stiffener between the retracted and extended positions.

7. The probe of claim 6, further comprising:
   an electrical based drive system that moves the stiffener between the retracted and extended positions.

8. The probe of claim 6, further comprising:
   a mechanical based drive system that moves the stiffener between the retracted and extended positions.

9. The probe of claim 6, further comprising:
   a handle affixed to the shaft, wherein in the stiffener actuator is located in the handle.

10. The probe of claim 1, further comprising:
    a channel in which the stiffener slides, wherein a first portion of the channel is located in the shaft and a second portion of the channel is located in the probe head; and
    a mechanical stop located at an end of the second portion, wherein the stiffener slides in the channel from the shaft, across the articulating member, into the probe head to the mechanical stop.

11. The probe of claim 1, wherein the stiffener is a non-flexible rod, non-flexible bar, or a tube.

12. The probe of claim 1,
    the probe head, further includes:
       at least one of a material free region or elongate channel; and
       a pre-loaded elastic device, which is attached to one of the stiffener and which holds the stiffener in the at least one of a material free region or elongate channel, and further comprising:
       an element affixed to another end of the stiffener and extending through the articulating member, the shaft and the handle,
       wherein the element, when held in the at least one of a material free region or elongate channel, allows articulation of the articulating member; and
       wherein the element is adapted to move in a direction from the probe to the handle, which pulls the stiffener into the articulating member against the pre-loading of the pre-loaded elastic device, which inhibits articulation of the articulating member.

13. The probe of claim 1, the probe head, further comprising:
    at least one of a material free region or elongate channel, which supports the stiffener; and
    a pre-loaded compression device, which urges the stiffener from the at least one of a material free region or elongate channel into the articulating member, which inhibits articulation of the articulating member.

14. A method, comprising:
    receiving, by a probe, an input that invokes the probe to transition between a first state in which a probe head with a transducer array articulates and a second state in which the probe head with the transducer array is inhibited from articulating; and
    moving, in response to the input, a non-flexible member located in the probe head from a fully retracted position where the non-flexible member is only in the head into an articulating member and shaft of the probe, thereby inhibiting the articulating member from articulating.

15. The method of claim 14, further comprising:
    moving a non-flexible member into an articulating member of the probe, thereby inhibiting the articulating member from articulating.

16. The method of claim 14, further comprising:
    moving a non-flexible member out of an articulating member of the probe, thereby allowing the articulating member to articulate.

17. The method of claim 14, wherein the non-flexible member is a rod or bar.

18. The method of claim 14, wherein the non-flexible member is a tube.

19. The method of claim 14, wherein the probe is an ultrasound probe of an ultrasound imaging system.

* * * * *